United States Patent [19]

Liu

[11] Patent Number: 4,835,338

[45] Date of Patent: May 30, 1989

[54] PROCESS FOR REMOVAL OF CARBONYL SULFIDE FROM ORGANIC LIQUID BY ADSORPTION USING ALUMINA ADSORBENT CAPABLE OF REGENERATION

[75] Inventor: Paul K. T. Liu, Pittsburgh, Pa.

[73] Assignee: Aluminum Company of America, Pittsburgh, Pa.

[21] Appl. No.: 91,176

[22] Filed: Aug. 31, 1987

[51] Int. Cl.$^4$ ............................................. C07C 7/12
[52] U.S. Cl. ................................. 585/823; 208/230; 208/235; 585/824
[58] Field of Search ............... 208/230, 235; 585/823, 585/824

[56] References Cited

U.S. PATENT DOCUMENTS

| | | | |
|---|---|---|---|
| 3,265,757 | 8/1966 | Fravel | 585/823 |
| 3,315,003 | 4/1967 | Khelghatian | 260/677 |
| 3,654,144 | 4/1972 | Collins | 208/245 |
| 3,812,200 | 5/1974 | Grey | 585/823 |
| 4,098,684 | 7/1978 | Innes | 208/245 |
| 4,290,879 | 9/1981 | Woodall | 208/235 |
| 4,391,677 | 7/1983 | Harris | 208/235 |
| 4,455,446 | 6/1984 | Brownell et al. | 585/850 |
| 4,491,516 | 1/1985 | Polleck | 208/248 |
| 4,613,724 | 9/1986 | Debras | 585/824 |

FOREIGN PATENT DOCUMENTS

| | | | |
|---|---|---|---|
| 0195534 | 9/1966 | European Pat. Off. | 585/824 |
| 3924945 | 11/1964 | Japan | 208/230 |

Primary Examiner—Asok Pal
Attorney, Agent, or Firm—Andrew Alexander; John P. Taylor

[57] ABSTRACT

An adsorption process is disclosed for removal of carbonyl sulfide (COS) from a liquid hydrocarbon which comprises providing an activated alumina adsorbent which has preferably impregnated with a compound selected from the class consisting of one or more alkali metal compounds, one or more alkaline earth metal compounds, or a mixture of such compounds; passing a liquid hydrocarbon containing COS through the activated alumina adsorbent at a flow rate sufficient to adsorb enough COS in the liquid hydrocarbon to lower the COS content of the liquid hydrocarbon to less than 1 ppm; monitoring the effluent liquid hydrocarbon to determine when the capacity of the adsorbent to adsorb the COS has been reached; and then regenerating the activated alumina adsorbent by passing a gas, heated to a temperature of from about 150° to about 300° C., through the adsorbent for a period of time sufficient to remove a substantial amount of the sulfur adsorbed thereon.

16 Claims, 1 Drawing Sheet

```
┌─────────────────────────────────────┐
│     FORMING AN ALKALI METAL-        │
│  IMPREGNATED ACTIVATED ALUMINA      │
│    ADSORBENT CONTAINING 3.0 TO      │
│       3.6 WT. % ALKALI METAL        │
└─────────────────────────────────────┘
                  │
                  ▼
┌─────────────────────────────────────┐
│   CONTACTING LIQUID HYDROCARBON     │
│    CONTAINING CARBONYL SULFIDE      │
│       WITH THE ADSORBENT TO         │
│    ADSORB THE CARBONYL SULFIDE      │
└─────────────────────────────────────┘
                  │
                  ▼
┌─────────────────────────────────────┐
│    MONITORING THE EFFLUENT TO       │
│  DETERMINE WHEN THE CARBONYL        │
│     SULFIDE LEVEL BEGINS TO         │
│        EXCEED ABOUT 1 PPM           │
└─────────────────────────────────────┘
                  │
                  ▼
┌─────────────────────────────────────┐
│    PASSING A GAS THROUGH THE        │
│    ADSORBENT AT 150 TO 300°C        │
│       FOR AT LEAST ONE HOUR         │
│    TO REGENERATE THE ADSORBENT      │
└─────────────────────────────────────┘
```

PROCESS FOR REMOVAL OF CARBONYL SULFIDE FROM ORGANIC LIQUID BY ADSORPTION USING ALUMINA ADSORBENT CAPABLE OF REGENERATION

BACKGROUND OF THE INVENTION 1. Field of the Invention

This invention relates to the removal of carbonyl sulfide from an organic liquid by selective adsorption of the carbonyl sulfide on an alumina adsorbent and the regeneration of the alumina adsorbent. 2. Description of the Related Art Carbonyl sulfide (COS) is an undesirable impurity in materials such as, for example, petroleum hydrocarbons because the COS is a sulfur source and therefore a potential atmospheric pollutant. COS also acts as an undesirable contaminant of industrial processes such as, for example, by poisoning of polymerization catalysts when the COS is present in petroleum-derived polymerizable olefins such as propylene. COS may be introduced into such processes as a contaminant initially present in the feedstock or it may be formed in the treating process as a result of the molecular sieve-catalyzed reaction of carbon dioxide with hydrogen sulfide or other sulfur compounds.

Depending upon the process and the required purity of the product, the COS level in the starting material may be required to be reduced to below 1 part per million by weight (ppmw) and sometimes to levels below 100 part per billion by weight (ppbw). Concentration of COS in the range of a few ppmw cannot be separated efficiently from a petroleum feedstock such as propylene by fractional distillation because the boiling point of COS differs from propylene by only 3.4° C.

Khelghatian U.S. Pat. No. 3,315,003 teaches a process for removing COS from a hydrocarbon by first contacting the hydrocarbon with a liquid such as monoethanolamine which scrubs the hydrocarbon to remove acid gases such as $H_2S$ and $CO_2$ and part of the COS. The hydrocarbon is then distilled. After several subsequent distillations, the liquid bottom product is treated with a soda-lime to remove any remaining COS.

However, separation of COS by processes which involve distillation, in addition, are extremely costly due to the cost of energy to vaporize virtually all of the liquid. It is, therefore, desirable to provide other means for the removal of COS impurities from organic liquids.

It has also been proposed to remove COS from hydrocarbons by catalytic hydrolysis to form $H_2S$, for example, using alumina as a catalyst. Frevel et al U.S. Pat. No. 3,265,757 teaches the hydrolysis of COS contained in a liquid hydrocarbon by contacting a mixture of the liquid hydrocarbon and water, at a temperature of from 20 to 50° C., with a high surface area alkaline, active alumina containing from 0.15 to 3 wt. % of sodium or potassium. The patentees state that the hydrolysis reaction will not commence, however, if the alumina is bone dry. They suggest either moistening the alumina catalyst with ion-free water prior to the reaction or passing a mixture of ion-free water and the liquid hydrocarbon through the catalyst bed until a sufficient amount of water has built up on the alumina to permit the hydrolysis reaction to proceed. However, while this process does remove COS (by converting it to $H_2S$), it does not remove sulfur per se from the hydrocarbon, but merely changes the form of the sulfur compound which still must be subsequently removed from the hydrocarbon by another process step.

In a later patent dealing with the same type of reaction, Polleck et al U.S. Pat. No. 4,491,516 teach that the reaction rate for the hydrolysis of COS with water over alumina may be greatly increased if the ratio of water to COS ranges from 1 to 10 moles of water per mole of COS, preferably 1.5 to 6 moles of water per mole of COS, or about 30% of saturation of the hydrocarbon, whichever upper limit provides the lesser amount of water.

Brownell et al U.S. Pat. No. 4,455,446 teaches the removal of COS from propylene by hydrolysis over a catalyst comprising platinum sulfide on alumina. The patentees state that the hydrolysis reaction may be carried out in either the gaseous or liquid phase with a temperature of 35 to 65° C. used for the liquid phase. An amount of water at least double the stoichiometric amount of the COS to be hydrolyzed must also be present.

Harris et al U.S. Pat. No. 4,391,677 describes a process for desulfurizing a butene-1 rich stock containing sulfurous impurities such as $H_2S$, COS, and $CH_3SH$. The process comprises passing the feed stream through a desulfurization zone maintained under desulfurization conditions and containing a charge of at least one desulfurization medium capable of adsorbing, absorbing, or converting $H_2S$, COS, and $CH_3SH$ to high boiling sulfurous compounds. The thus-treated feed stream, now essentially free from $H_2S$, COS, and $CH_3SH$, is then passed to a distillation zone, and recovered as a bottom product as a butene-2 rich stream containing high boiling sulfurous compounds. The desulfurization zone comprises a bed of activated alumina followed by a bed of zinc oxide. The activated alumina is said to hydrolyze COS in the presence of 20 to 1000 ppm of water to $H_2S$ and partially to remove $H_2S$ and methyl mercaptans. The zinc oxide is said to remove all the $H_2S$ and methyl mercaptan not removed by the alumina bed.

COS has also been removed from liquid hydrocarbons by adsorption on a zeolite adsorbent. Collins U.S. Pat. No. 3,654,144 discloses removing COS by adsorbing it on a particular modified zeolite A adsorbent comprising an alkali metal cation form of zeolite A which has been ion-exchanged with alkaline earth metal cations, preferably calcium cations, to the extent of from 20 to about 100 equivalent percent.

Innes U.S. Pat. No. 4,098,684 describes the removal of COS and other sulfur compounds by passing them through a dual bed of zeolites comprising, respectively, a 13X molecular sieve, and a zeolite A sieve having a pore size of 4 Angstroms. The commercially available 13X zeolite is said to remove any $H_2S$ and mercaptans present. The capacity for COS adsorption by the 13X sieve is said to be small. The 13X zeolite is described as a three dimensional network with mutually connected intracrystalline voids accessible through pore openings which will admit molecules with critical dimensions up to 10 Angstroms and having the general chemical formula: $0.83 \pm 0.05\ Na_2O/1.00\ Al_2O_3/2.48 \pm 0.038\ SiO_2$. The molecular sieve beds may be regenerated by passing a hot, substantially nonadsorbable, purge gas through the beds at a temperature of about 177° to 316° C. (350° to 600° F.).

While zeolite materials have thus been used as adsorbing agents to remove sulfurous compounds such as COS from liquid hydrocarbons, it has been found that zeolite, with its cage structure, has a low adsorption rate at ambient temperature and is, therefore, not practical for treating liquid at such temperatures.

It would, therefore, be highly desirable to provide a process for the removal of sulfurous impurities such as COS from liquid hydrocarbons, preferably in the absence of water, using an alumina adsorbent having high adsorption characteristics yet capable of being regenerated without substantial loss of adsorption capability.

SUMMARY OF THE INVENTION

It is, therefore, an object of this invention to provide an improved process for the removal of carbonyl sulfide from a liquid hydrocarbon by adsorption on an adsorption media comprising an activated alumina adsorbent followed by regeneration of the activated alumina after the adsorption capacity has been reached.

It is another object of this invention to provide an improved process for the removal of carbonyl sulfide (COS) from a liquid hydrocarbon which comprises adsorbing the COS on an adsorption media comprising an activated alumina which has been previously treated with one or more alkali metal compounds, one or more alkaline earth metal compounds, and a mixture thereof; and then regenerating the adsorbent after the adsorption capacity has been reached.

It is yet another object of this invention to provide an activated alumina which has been used to adsorb carbonyl sulfide thereon from a hydrocarbon and then regenerated by passing a gas through the adsorbent.

It is a further object of this invention to provide an activated alumina adsorbent which has been pretreated with a compound selected from the class consisting of one or more alkali metal compounds, one or more alkaline earth metal compounds, or mixtures of any two or more of such compounds; then used to adsorb carbonyl sulfide thereon from a hydrocarbon; and then regenerated by passing a gas through the adsorbent.

These and other objects of the invention will be apparent from the following description and accompanying flow sheet.

BRIEF DESCRIPTION OF THE DRAWINGS

The sole drawing is a flow sheet illustrating the process of the invention.

DETAILED DESCRIPTION OF THE INVENTION

The invention comprises an improved process for removal of carbonyl sulfide (COS) from liquid hydrocarbons by adsorption on an activated alumina adsorbent and then regenerating the adsorbent when the capacity has been reached and a regenerated activated alumina adsorbent which has been regenerated by flowing a gas through the activated alumina after the adsorbent has been used to adsorb COS thereon from a hydrocarbon liquid.

The activated alumina adsorbent used in the process of the invention may comprise a commercially available activated alumina such as, for example, S-100, available from the Aluminum Company of America, having a particle size range of from about ¼" to about 100 mesh (U.S. Series). The average pore size of the alumina particles ranges from about 10 Angstroms to about 10,000 Angstroms.

The activated alumina, may be activated by heating to a temperature of at least about 300° C. or higher, e.g., 450° C.

The activated alumina preferably is impregnated with one or more alkali metal compounds, one or more alkaline earth metal compounds, or a mixture thereof in an amount which may range from about 0.01 to about 10 wt. %, preferably from about 0.01 to about 5.0 wt. %, more preferably from about 2.0 to about 4.0 wt. %, and most preferably from about 2.5 to about 3.5 wt. %, wherein the wt. % is measured as the percentage weight of the impregnated alkali metal or alkaline earth metal to the total weight of alkali metal/alkaline earth metal and aluminum in the adsorbent, e.g., 3.3 wt. % Na/Al. The alkali metal compound or alkaline earth metal compound preferably will comprise a material with a decomposable anion so that no undesirable other materials are left in the alumina after the impregnation. Examples of such alkali metal/alkaline earth metal compounds include, for example, the hydroxides, carbonates, and nitrates of sodium, potassium, lithium, calcium, and magnesium.

The activated alumina may be impregnated by the alkali metal/alkaline earth metal compound by soaking the activated alumina for at least about 5 minutes up to 1 hour or longer in an aqueous solution containing the dissolved alkali metal/alkaline earth metal compound and then drying the impregnated alumina and reactivating it. More than one cycle of impregnation and drying may be used, if desired. The compound may also be applied to the activated alumina by spraying or the like, if desired.

The process is capable of treating a liquid hydrocarbon containing an impurity concentration of COS of as much as 200 ppm and reducing the concentration down to below 1 ppm. Since the removal of COS from a liquid hydrocarbon containing COS impurities therein is principally via adsorption, the presence or absence of any specific amounts of moisture in the hydrocarbon is not critical to the operation of the process. However, since it has been found that the capacity of the adsorbent for COS varies inversely with the amount of water present, it is preferred to operate with as little water present as possible. For example, when the solution contained 27 ppm (by weight) water, the total amount of sulfur adsorbed was 2.0 wt. % of sulfur. However, when the solution contained 110 ppm water, the total amount of sulfur adsorbed on the same amount of adsorbent decreased to 1.7 wt. % of sulfur. It should also be noted that no water need be present for the adsorption process to operate successfully.

If desired, in a preferred embodiment, the hydrocarbon liquid to be purified may be first passed through a drying bed such as a molecular sieve or silica or the like to remove most if not all of the moisture present prior to passing the hydrocarbon liquid through the adsorbent to avoid the reduction in adsorption capacity just discussed above.

If moisture is present in the hydrocarbon liquid, some of the COS may be converted by hydrolysis to H$_2$S and other reaction products which may then be adsorbed onto the alkali metal-impregnated activated alumina adsorbent. Such adsorbed reaction products may then be removed, along with the adsorbed COS, upon subsequent regeneration of the adsorbent.

The adsorption process may be carried out at ambient temperature, although temperatures of from 15 to 100° C may be used if convenient, e.g., if the liquid hydrocarbon is at this temperature from previous processing, it need not be heated or cooled prior to passing through the adsorbent.

The adsorption may be advantageously carried out in a packed column although any other convenient form of maintaining contact between the adsorbent and the liquid hydrocarbon may be employed such as a slurry process. The flow rate of the liquid hydrocarbon through the adsorbent should be sufficiently slow to permit a sufficient contact time to permit the desired adsorption of the COS in the liquid hydrocarbon onto the alkali metal/ alkaline earth metal-impregnated activated alumina to occur. The actual amount of contact time will vary with the particle size of the adsorbent.

The adsorption capacity of the alkali metal/alkaline earth metal-impregnated activated alumina adsorbent is determined by monitoring the sulfur content of the effluent from the adsorbent. Prior to reaching its adsorption capacity, the effluent will contain less than 1 ppm sulfur. After such monitoring indicates that the capacity of the adsorbent has been reached, i.e., by a rise in the sulfur content of the effluent, the adsorbent may be regenerated by passing a heated gas such as air, hydrocarbon gases, or nitrogen or other inert gases through the adsorbent. The heated gas is preferably heated to a temperature of from about 100° to 300° C., more preferably about 150° to 250° C., and most preferably about 250° C., and passed through the adsorbent at a rate of about 1 to 10 cc/min. until a substantial amount of the sulfur adsorbed thereon is removed. By a substantial amount is meant about 40 wt. % or higher of the adsorbed sulfur. This can easily be determined by analyzing for the amount of residual sulfur in the adsorbent. The direction of flow of the regenerating gas through the adsorbent may be either in the same direction as the liquid hydrocarbon flow, e.g., when the adsorbent is packed in a column, or the regenerating gas may be passed through the adsorbent in a direction counter to the normal flow of liquid hydrocarbon therethrough.

The following examples will serve to better illustrate the process of the invention.

EXAMPLE 1

Two ¼" diameter by 7 cm columns were packed with 1.10 grams each of an activated alumina adsorbent having an average particle size of about −325 mesh (Tyler). One of the columns was packed with alkali metal-impregnated activated alumina containing 3.3 wt. % Na/Al and the other column was packed with an unimpregnated activated alumina adsorbent. In each instance, a liquid propylene feed containing 104 ppm COS was passed through the respective column at a flow rate of 2 cc/min. In contrast to the prior art, no water was present in the feed stream to either column. The effluent was monitored for total sulfur concentration and, in both instances, the removal was sufficient to provide a total sulfur concentration in the effluent of less than 1 ppm. The breaktime, however, indicative of the adsorption capacity of the adsorbent after which the effluent contained higher amounts of total sulfur concentration, was 50 minutes for the unimpregnated activated alumina adsorbent and 125 minutes for the alkali metal-impregnated activated alumina adsorbent, thus indicating that the alkali metal-impregnated activated alumina has a much higher adsorption capacity for COS than the unimpregnated activated alumina adsorbent.

EXAMPLE 2

Two ¼" diameter by 5 cm columns were packed with an activated alumina adsorbent having an average particle size of about -325 mesh (Tyler). One of the columns was packed with 0.70 grams of an alkali metal-impregnated activated alumina containing 3.3 wt. % Na/Al and the other column was packed with 0.68 grams of an unimpregnated activated alumina adsorbent. In each instance, a liquid hexane feed containing 32 ppm COS was passed through the respective column at a flow rate of 0.5 cc/min. In each instance, the feed solution passing through the column had a moisture content of 100 ppm water.

The effluent was monitored for total sulfur concentration and, in both instances, the removal was again sufficient to provide a total sulfur concentration in the effluent of less than 1 ppm.

After the adsorbents in each of the columns had reached their adsorption capacity, the columns were analyzed to determine the total amount of sulfur adsorbed on the respective columns. The amount of sulfur adsorbed by the unimpregnated adsorbent was 1.5 wt. % sulfur per gram of alumina and the amount of sulfur adsorbed by the alkali metal-impregnated alumina was 1.6 wt. % sulfur per gram of alumina.

The respective adsorbents were regenerated by passing air, heated to a temperature of 250° C, through the columns for about 2 hours at a rate of 5.0 cc/min.

The adsorbents were again tested by passing the same respective feed solutions through the columns and then analyzing the respective columns after monitoring of the effluent from each column indicated that the adsorption capacity of the respective adsorbent had again been reached. The regenerated unimpregnated activated alumina was found to have an adsorption capacity of about 0.1 wt. % sulfur per gram of alumina while the regenerated alkali metal-impregnated alumina was found to have a capacity of 0.8 wt. % sulfur per gram of alumina, thus indicating the superior regenerating capabilities of alkali metal-impregnated activated alumina.

The alkali metal-impregnated activated alumina adsorbent was again tested by regenerating it for the second time under the same conditions as the previous regeneration. The same liquid hydrocarbon was then again passed through the column until capacity was again reached. The column was then analyzed again to determine the amount of sulfur adsorption thereon.

The amount of sulfur adsorbed, after two regenerations, was found to be 0.67 wt. % sulfur per gram of alumina, indicating that the alkali metal-impregnated activated alumina is capable of not only adsorbing COS from a hydrocarbon liquid, but also capable of being regenerated successfully for use a number of times compared to conventional activated alumina.

EXAMPLE 3

To illustrate the adsorption capabilities of the process when purifying liquid hydrocarbons having a range of COS impurity concentrations therein, 3 adsorption columns were prepared, each having a column length of 5 cm and an ID of ¼" and each packed with 0.80 grams of an activated alumina impregnated with 3.3 wt. % Na/Al. Three feed solutions of n-hexane were fed through the respective columns, each containing a different amount of COS. In each instance, the moisture content of the n-hexane was 27 ppm. After each column became completely saturated with sulfur, as indicated by monitoring of the effluent for sulfur content over 1 ppm, each column was analyzed to determine total sulfur adsorbed. Each column was then regenerated by passing nitrogen, heated to 275° C., through the column for 2 hours at a rate of 3.0 cc/min.

After each column was regenerated, n-hexane, containing the same respective concentration of COS, was again passed through the column until saturation was reached. Each column was again analyzed for sulfur content. The results, as shown in Table I below, indicate that the alkali metal-impregnated activated alumina adsorbent is capable of adsorbing COS from liquid hydrocarbons in a wide range of concentrations even after regeneration of the adsorbent.

TABLE I

| Sample Number | COS Conc. in Feed (ppm) | Initial Sulfur Adsorption (wt. % S/gram Al) | Sulfur Adsorption After Regeneration (wt. % S/gram Al) |
| --- | --- | --- | --- |
| 1 | 50.2 | 1.9 | 0.9 |
| 2 | 94.2 | 2.1 | 0.95 |
| 3 | 156.9 | 2.1 | 0.95 |

To further illustrate the adsorption capabilities of the process when purifying liquid hydrocarbons having COS impurities therein after the adsorbent has been regenerated a number of times, an adsorption column was prepared having an ID of ¼" and packed with 5 cm of activated alumina particles of −100 to +200 mesh which were impregnated with 5.0 wt. % Na. A feed solution of n-hexane, containing 20 ppm of COS and about 100 ppm water, was fed through the column at a rate of about 0.5 cc/min. After the column became completely saturated with sulfur, as indicated by monitoring of the effluent for sulfur content over 1 ppm, the column was analyzed to determine total sulfur adsorbed. The column was then regenerated by passing nitrogen, heated to 250° C., through the column for 2 hours at a rate of 3.0 cc/min.

After the column was regenerated, n-hexane, containing the same concentration of COS, was again passed through the column until saturation was reached. The column was again analyzed for sulfur content. This procedure was repeated two further times resulting in three regenerations of the adsorbent. The results, as shown in Table II below, indicate that the alkali metal-impregnated activated alumina adsorbent is capable of adsorbing COS from liquid hydrocarbons even after repeated regeneration of the adsorbent.

TABLE II

| Run | Weight Percent of Sulfur Adsorbed | Number of Regenerations |
| --- | --- | --- |
| 1 | 1.95 | 0 |
| 2 | 0.95 | 1 |
| 3 | 0.7 | 2 |
| 4 | 0.6 | 3 |

To further illustrate the adsorption capabilities of the process when purifying liquid hydrocarbons having COS impurities therein, using an activated alumina adsorbent impregnated with varying amounts of an alkali metal, three adsorption columns were prepared, each having an ID of ¼" and packed with 5 cm of activated alumina particles of −100 to +200 mesh. The activated alumina adsorbent in the three columns were respectively impregnated with 0, 3.0, and 5.0 wt. % Na. A feed solution of n-hexane, containing 20 ppm of COS and about 100 ppm water, was fed through each column at a rate of about 0.5 cc/min. After the columns became completely saturated with sulfur, as indicated by monitoring of the effluent for sulfur content over 1 ppm, each column was analyzed to determine total sulfur adsorbed.

The results, as shown in Table III below, indicate higher adsorption capacity for sulfur with higher amounts of alkali metal impregnation.

TABLE III

| Weight Percent of Adsorbed Sulfur on Column | Weight Percent of Alkali Metal Impregnation |
| --- | --- |
| 0 | 1.5 |
| 3.0 | 1.63 |
| 5.0 | 1.92 |

Thus, the process of the invention provides for the purification of a liquid hydrocarbon to remove COS therefrom by adsorption on an alkali metal-impregnated activated alumina capable of being regenerated for reuse. Since removal of the COS is principally by adsorption rather than by hydrolysis, there is no need to maintain critical ratios of water/COS content in the liquid hydrocarbon nor is there any need to wet the alumina or to pass initial amounts of water through the adsorbent to initiate the adsorption as is taught in the hydrolysis processes for catalytic removal of COS from liquid hydrocarbons with alkali metal-impregnated activated alumina catalysts.

Having thus described the invention, what is claimed is:

1. A process for removal of carbonyl sulfide (COS) from a liquid hydrocarbon by adsorption which comprises:
    (a) contacting a liquid hydrocarbon containing COS with an activated alumina adsorbent impregnated with from 0.1 to 10 wt. % of a metal compound, based on the weight ration of the metal in said compound to alumina in said adsorbent, selected from the class consisting of one or more alkali metal compounds, one or more alkaline earth metal compounds, or a mixture of such compounds to adsorb the COS in the liquid hydrocarbon for a period of time sufficient to lower the COS content of the liquid hydrocarbon to less than 1 ppm; and
    (b) regenerating the activated alumina adsorbent by passing a heated gas through the adsorbent to remove a substantial amount of sulfur adsorbed thereon.

2. The process of claim 1 wherein said range of said impregnated compound is from about 0.01 to about 5.0 wt. %.

3. The process of claim 2 wherein said range of said impregnated compound is from about 2.0 to 4.0 wt. %.

4. The process of claim 3 wherein said range of said impregnated compound is from about 2.5 to 3.5 wt. %.

5. The process of claim 4 wherein said activated alumina contains about 3.3 wt. % of said impregnated compound.

6. The process of claim 4 wherein the metal in said metal compound impregnated in said activated alumina adsorbent consists essentially of sodium.

7. The process of claim 1 wherein said hydrocarbon liquid containing COS contains 100 ppm water or less.

8. The process of claim 1 wherein said hydrocarbon liquid containing COS contains less than 20 ppm water.

9. A process for removal of carbonyl sulfide (COS) from a liquid hydrocarbon by adsorption which comprises:
    (a) forming an impregnated activated alumina adsorbent by impregnating an activated alumina material with a metal compound selected from the class consisting of one or more alkali metal compounds, one or more alkaline earth metal compounds, or a mixture of such compounds in an amount sufficient to provide a wt. % ratio, based on the weight ratio of the metal in said impregnated compound to aluminum in said adsorbent, of from about 0.01 to 10 wt. %;

(b) passing a liquid hydrocarbon containing COS through a packed column containing said impregnated activated alumina adsorbent at a flow rate sufficient to permit enough COS in said liquid hydrocarbon to be adsorbed by said impregnated activated alumina adsorbent to lower the COS content of said liquid hydrocarbon to less than 1 ppm;

(c) monitoring the effluent liquid hydrocarbon to determine when the capacity of said adsorbent to adsorb said COS has been reached; and (d) regenerating said impregnated activated alumina adsorbent by passing a gas, heated to a temperature of from about 150° to about 300° C., through the adsorbent for a period of time sufficient to remove at least 40 wt. % of the sulfur adsorbed thereon.

10. The process of claim 9 wherein said range of said impregnated compound is from about 0.01 to about 5.0 wt. %.

11. The process of claim 10 wherein said step of impregnating said activated alumina with said metal compound further comprises impregnating said activated alumina with a metal compound containing sodium.

12. The process of claim 10 wherein said step of impregnating said activated alumina with said metal compound further comprises impregnating said activated alumina with a metal compound containing potassium.

13. The process of claim 10 wherein said step of impregnating said activated alumina with said metal compound further comprises impregnating said activated alumina with a metal compound containing lithium.

14. The process of claim 10 wherein said step of impregnating said activated alumina with said metal compound further comprises impregnating said activated alumina with a metal compound containing calcium.

15. The process of claim 10 wherein said step of impregnating said activated alumina with said metal compound further comprises impregnating said activated alumina with a metal compound containing magnesium.

16. A regenerated activated alumina adsorbent capable of adsorbing carbonyl sulfide (COS) from a liquid hydrocarbon by adsorption comprising a material which has been impregnated with from about 0.1 to about 5 wt. % of a metal compound selected from the class consisting of one or more alkali metal compounds, one or more-alkaline earth metal compounds, or a mixture of such compounds and which has been previously contacted with a liquid hydrocarbon containing COS to permit adsorbtion of the COS thereon and then regenerated by passing a heated gas through the adsorbent to remove a substantial amount of the sulfur adsorbed thereon.

* * * * *